US007807369B2

(12) United States Patent
van der Burg et al.

(10) Patent No.: US 7,807,369 B2
(45) Date of Patent: Oct. 5, 2010

(54) METHODS AND MEANS FOR THE TREATMENT OF HPV INDUCED INTRAEPITHELIAL NEOPLASIA

(75) Inventors: Sjoerd Hendricus van der Burg, Waddinxveen (NL); Rienk Offringa, Leiden (NL); Cornelis Johannes Maria Melief, Haarlem (NL); Theodorus Jozef Maria Helmerhorst, Amsterdam (NL)

(73) Assignee: Leiden University Medical Center, Leiden (NL)

( * ) Notice: Subject to any disclaimer, the term of this patent is extended or adjusted under 35 U.S.C. 154(b) by 0 days.

(21) Appl. No.: 11/912,961

(22) PCT Filed: Apr. 25, 2006

(86) PCT No.: PCT/NL2006/050099

§ 371 (c)(1),
(2), (4) Date: Apr. 25, 2008

(87) PCT Pub. No.: WO2006/115413

PCT Pub. Date: Nov. 2, 2006

(65) Prior Publication Data

US 2009/0060870 A1    Mar. 5, 2009

(30) Foreign Application Priority Data

Apr. 27, 2005  (EP)  ................... 05103447

(51) Int. Cl.
*C12Q 1/68* (2006.01)

(52) U.S. Cl. ......................................................... 435/6
(58) Field of Classification Search ...................... 435/6
See application file for complete search history.

(56) References Cited

U.S. PATENT DOCUMENTS

| | | | |
|---|---|---|---|
| 6,524,825 B1 * | 2/2003 | Mizzen et al. | 435/69.7 |
| 7,211,411 B2 * | 5/2007 | Neefe et al. | 435/69.1 |
| 7,262,014 B2 * | 8/2007 | Mizzen et al. | 435/6 |
| 2003/0161811 A1 * | 8/2003 | Chandrasekher et al. | 424/85.2 |
| 2004/0235741 A1 * | 11/2004 | Neefe et al. | 514/12 |
| 2007/0134273 A1 * | 6/2007 | Romagne et al. | 424/248.1 |

FOREIGN PATENT DOCUMENTS

| | | |
|---|---|---|
| EP | 1 288 292 A1 | 3/2003 |
| WO | WO 00/40228 | 7/2000 |
| WO | WO 02/070004 A2 | 9/2002 |
| WO | WO 2005/020995 A1 | 3/2005 |

OTHER PUBLICATIONS

Van Poelgeest, M. et al. "Detection of Human Papillomavirus (HPV) 16-Specific CD4+ T-cell Immunity in Patients with Persistent HPV16-Induced Vulvar Intraepithelial Neoplasia in Relation to Clinical Impact of Imiquimod Treatment." *Clin Cancer Res*, 2005, 11:5273-5280.
Todd, RW. et al. "Detection of CD8+ T cell Responses to Human Papillomavirus Type 16 Antigens in Women Using Imiquimod as a Treatment for High-Grade Vulval Intraepithelial Neoplasia." *Gynecologic Oncol*, 2004, 92:167-74.
De Jong, A. et al. "Human Papillomavirus Type 16-Positive Cervical Cancer is Associated with Impaired CD4+ T-Cell Immunity Against Early Antigens E2 and E6." *Cancer Res.*, 2004, 64:5449-55.
De Jong, A et al. "Frequent Detection of Human Papillomavirus 16 E2-specific T-helper Immunity in Healthy Subjects." *Cancer Res*, 2002, 62:472-479.
Van Der Burg, SH et al. "Natural T-Helper Immunity Against Human Papillomavirus Type 16 (HPV16) E7-Derived Peptide Epitopes in Patients with HPV16-Positive Cervical Lesions: Identification of 3 Human Leukocyte Antigen Class II Restricted Epitopes." *Int'l J Cancer*, 2001, 91:612-18.
Sauder, DN. "Imiquimod: Modes of Action." *Brit J. Dermatol*, 2003, 149 (Suppl. 66): 5-8.
Stanley, M.A. "Imiquimod and the Imidazoquinolones: Mechanism of Action and Therapeutic Potential." Clin Exper Dermatol, 2002, 27:571-57.
P. J. de Vos van Steenwijk, et al., Surgery followed by Persistence of High-Grade Squamous Intraepithelial Lesions Is Associated with the Induction of a Dysfunctional HPV16-Specific T-Cell Response *Clin Cancer Res* 14:7188-7195 (2008).

* cited by examiner

*Primary Examiner*—Ali R. Salimi
(74) *Attorney, Agent, or Firm*—Browdy and Neimark, PLLC

(57) ABSTRACT

The current invention provides improved methods and means for the treatment of virally induced intraepithelial neoplasias of the ano-genital tract, such as HPV induced vulvar-, cervical-, vaginal-, penile- and anal intraepithelial neoplasias (VIN, CIN, VAIN, PIN and AIN). The invention provides a method of treatment of a subject suffering from an anogenital intraepithelial neoplasia comprising at least the steps of first determining whether the subject has a T-cell reactivity for viral early antigens, in particular high risk type HPV antigens; and subsequently a local treatment of the neoplasia with immune modulating compounds eliciting local inflammation if the subject scores positive for the T-cell reactivity, preferably a CD4+response against HPV early antigens. The invention also comprises methods and means to induce or further stimulate a cellular immune response against HPV antigens, prior to or during treatment with the immune modulating compound capable of eliciting a local inflammatory response.

11 Claims, 3 Drawing Sheets

METHODS AND MEANS FOR THE TREATMENT OF HPV INDUCED INTRAEPITHELIAL NEOPLASIA

FIELD OF THE INVENTION

Figure 1A:
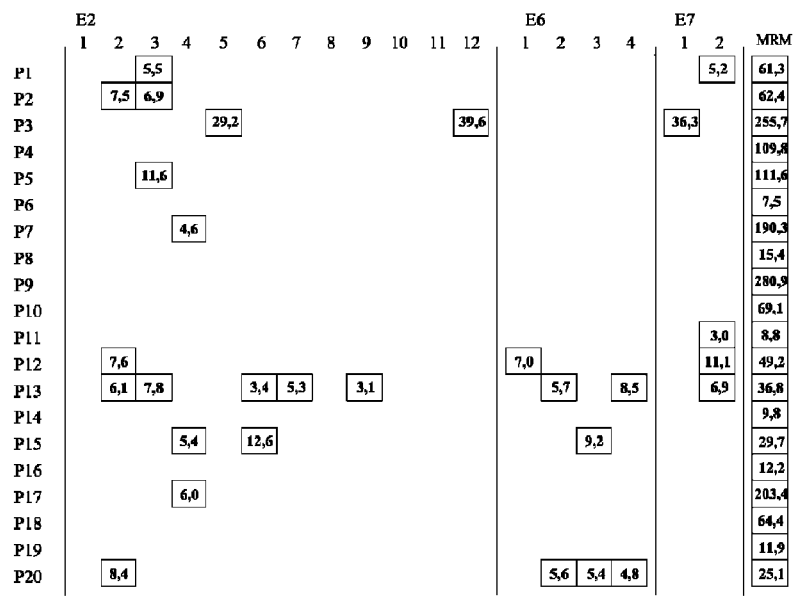

The current invention relates to the field of medicine, in particular to the areas of immuno-modulation, immunotherapy and prophylaxis of HPV infections and neoplastic disease.

BACKGROUND OF THE INVENTION

Anogenital tract infections with high-risk human papillomaviruses (HPV) are very common (1-3), causing lesions in, on and/or around the areas of the anus, rectum, penis, vulva, vagina and cervix. Fortunately, the majority of infected subjects clear the infection (4; 5). A persistent infection with a high risk HPV, mostly HPV16, can lead to neoplasia of the anogenital tract, of which cervical intraepithelial neoplasia (CIN) and cervical carcinoma are the most well-known (6; 7). HPV16 infection may also cause a chronic skin disorder of a) the vulva known as vulvar intraepithelial neoplasia (VIN) (8-10), b) the anus called anal intraepithelial neoplasia (AIN), c) the vagina designated as VAIN and d) the penis known as PIN. In contrast to CIN, which in general is effectively treated by eradication of the area involved, these other disease have a chronic nature with high relapse rates after standard treatments (11-13).

The use of immune modifiers, causing inflammatory reactions, have been applied for the treatment of VIN. In particular Imiquimod therapy has been put forward as an alternative approach for the treatment of VIN. Chemically, imiquimod is 1-(2-methylpropyl)-1H-imidazo[4,5-c]quinolin-4-amine. This immune response modifier acts through Toll-like receptor 7 of the innate immune system resulting in the secretion of a multitude of proinflammatory cytokines, among which interferon. There is recent evidence that imiquimod also possesses direct pro-apoptotic activity against tumor cells (14-16). Topical application preserves the anatomy and function of the vulva while surgical excision or ablation of affected skin may be extensive and disfiguring and can carry considerable psychosexual morbidity. Clinical success rates differ and are estimated on 30-87% (17-21).

The HPV16 early antigens E2, E6 and E7 are among the first of proteins that are expressed in HPV-infected epithelia. Previous studies on HPV-specific T-cell immunity against these early antigens showed that type 1 (IFN-$\gamma$) T-cell memory against the early antigens can be detected in the majority of healthy sexually active individuals, but is weak or absent in patients with HPV16-induced cervical neoplasia (22-24). In combination with earlier reports that point at a role for CD4+ T-cells in the protection against progressive HPV-infection (reviewed in 25), data argue that CD4+ type 1 T-cell response against the early antigens of HPV16 may play an important role in the protection against progressive HPV16-induced disease.

The goal of the current invention is therefore to provide improved methods and means for the treatment of virally induced intraepithelial neoplasias of the ano-genital tract, such as VIN, CIN, VAIN, PIN and AIN.

SUMMARY OF THE INVENTION

The invention achieves its goal by examining whether a subject has developed an immune response against viral early antigens. The current invention demonstrates a decisive role of HPV-specific T cell immunity in the success or failure of treatment with immune modifiers causing local inflammation such as TLR activating compound like Imiquimod. The specification provides a detailed analysis with respect to the magnitude and cytokine polarization of the HPV16-specific CD4+ T-cell response in patients with high grade VIN. The invention demonstrates that chronic exposure of the immune system to the HPV viral proteins results in the induction of interferon gamma (IFN$\gamma$) T-cell immunity in about half of the patients. Importantly, the presence of these type 1 (IFN$\gamma$) T-cell responses is associated with a favourable clinical response to treatment with immune modifiers, such as imiquimod that is used in this example. Implications of the invention are that for effective treatment with immune modifiers causing local inflammation, an immune response against HPV early antigens should first be determined. If absent, an immune response against HPV early antigens may be raised via methods known in the art, in order to achieve optimal results from treatment with immune modifying compounds causing local inflammatory responses. Since the use of immune modifiers such as imiquimod is demonstrated to be much less or not effective in individuals not having an CD4+ T-cell response against viral early antigens, this group of subjects may first be treated with medicaments in order to elicit a T-cell response against viral antigens. If this is not sufficiently successful, refractory individuals are preferably treated by other means which may be more effective, such as surgical excision or ablation of affected skin or alternative medication. Moreover, the negative side effects of treatment with immune modifiers causing local inflammation, such as itching, burning and pain, may be avoided for the group of subjects wherein these compounds and/or compositions are less effective or even ineffective, due to the absence of an immune response against viral early antigens.

DETAILED DESCRIPTION OF THE INVENTION

In a first embodiment, the current invention provides a method of treatment of a subject suffering from an anogenital intraepithelial neoplasia comprising at least the steps of:

i) determining whether the subject has T-cell reactivity for viral antigens; and ii) subsequent local treatment of the neoplasia with immune modulating compounds eliciting local inflammation, in a patient scoring positive for T-cell reactivity against HPV antigens in step i).

T-cell reactivity to viral antigens, in particular to HPV early antigens, more in particular HPV E2, E6 and E7 proteins from high risk types, such as HPV 16, HPV 18 and HPV 33, may be determined on blood samples and isolated cells therefrom, using standard assays such as those described in the examples section of this specification and/or in WO 02/070006 (incorporated herein by reference), T-cell proliferation assays, INF$\gamma$ ELISPOT assays, cytokine multiplex assays or ELISA assays. In particular a CD4+ T cell response producing IFN$\gamma$ (type 1 T-cell response) is shown here to be highly beneficial for the local treatment of ano-genital tract intraepithelial neoplasias with immune modifiers. A CD4+ immune response against viral early antigens or epitopes bound on MHC class II molecules is in particular advantageous. Part of the invention is the activation of professional antigen presenting cells such as dendritic cells, macrophages and NK cells, which are useful for eliciting an effective local inflammatory reaction against virally infected cells and/or neoplasias in the anogenital area.

A CD8+ cytotoxic T cell response, responding to MHC class I bound viral epitopes, may further enhance an effective immune response against HPV infected cells, in particular in the anogenital epithelia.

Preferably the immune response and local inflammation induced in the method of the invention by the application of immune modifying compounds, preferably immune modifying compounds that are capable of inducing local inflammation and/or eliciting a local inflammatory response. Most preferably an immune modifying compound or composition to be used according to the invention is capable of activation of the innate immune system, which can be activated particularly well via Toll like receptors (TLR's), including e.g. TLR's 1 to 10. Compounds capable of activating TLR receptors and modifications and derivatives thereof may be used for inducing a local inflammatory response and are well documented in the art (ref. 51). TLR1 may be activated by bacterial lipoproteins and acetylated forms thereof, TLR2 may in addition be activated by Gram positive bacterial glycolipids, LPS, LPA, LTA, fimbriae, outer membrane proteins, heatshock proteins from bacteria or from the host, and Mycobacterial lipoarabinomannans. TLR3 may be activated by dsRNA, in particular of viral origin, or by the chemical compound poly (I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B *Streptococcus* heat labile soluble factor (GBS-F) or *Staphylococcus* modulins. TLR7 may be activated by imidazoquinolines. TLR9 may be activated by unmethylated CpG DNA or chromatin-IgG complexes.

In particular TLR3, TLR7 and TLR9 play an important role in mediating an innate immune response against viral infections, and compounds capable of activating these receptors are particularly preferred for use in the methods of local treatment and in the compositions or medicaments according to the invention. Particularly preferred compounds comprise, but are not limited to, dsRNA, poly(I:C), unmethylated CpG DNA which trigger TLR3 and TLR9 receptors. Most preferably TLR7 activating compounds are used in this invention, comprising compounds such as Imidazoquinolines (examples: Imiquimod and/or R-848/resiquimod), loxoribine (7-allyl-8-oxoguanosine) and bropirimine (2-amin-5-allyl-8-oxoguanosine), which have been shown to have potent immuno-stimulatory and antiviral activities and are capable of inducing proinflammatory cytokines such as IFN-α, TNF-α, IL-6 and/or IL-12.

Other compounds that may be applied in the method and pharmaceutical compositions or medicaments according to the invention to stimulate or to further enhance a local inflammatory response comprise chemokines and cytokines that are members of the inflammatory pathway. Examples are the type I interferons (interferon α and β) and the cytokines, IL-1, TNF-α, IL-6, IL-8 (CXCL8) and IL-12 and/or the chemokines CXCL-1, 2, 3, 7, 8, 10, 12, 13; CCL-2, 3, 4, 5, 11, 18, 20, 27; XCL-1 and CX3CL-1.

The methods of treatment and the pharmaceutical compositions according to the invention are particularly suitable for the treatment of anogenital intraepithelial neoplasias induced by viral infections, in particular Human Papilloma Virus (HPV) infections, more in particular of the high risk types, comprising HPV-16, 18, 31, 33, 35, 39, 45, 51, 52, 56, 58, 59, and 68 types. However, also other infections or co-infections in these epithelial regions with (myco)bacteria, fungi and/or other viruses, such as Herpes viruses (HSV-1, HSV-2), HIV and/or Cytomegalovirus (CMV), resulting from failure of the immunesystem to protect against, may be successfully treated by the methods and the medicaments according to this invention. The invention is suitable for treatment of any mammal which can be (co-)infected with HPV, HSV and CMV viruses, and is most suitable for use on human subjects and/or patients.

The neoplasia to be treated with the methods and medicaments according to the current invention may be any HPV induced neoplasia, preferably in an epithelial tissue, in the ano-genital area and/or ano-genital tract, comprising the vulva, vagina, cervix, penis, scrotum, anus and rectum. The neoplastic disorders to be treated comprise Cervical Intraepithelial Neoplasia of various grades (CIN I, II and III), Vulvar intraepithelial neoplasias of various grades (VIN, II and III) and Vaginal intraepithelial neoplasias (VAIN) and anal intraepithelial neoplasia (AIN). Also male subjects suffering from virally induced neoplasias in the ano-genital area and/or tract, such as but not limited to, Penile intraepithelial neoplasia (PIN) and Anal intraepithelial neoplasia (AIN), may be treated according to this invention.

In a particularly preferred embodiment the current invention comprises a step to elicit (de novo) or to enhance a (pre-existing) immune response against a viral infection. A T cell response, and in particular a CD4+ T cell response, is shown to be particularly advantageous for the methods according to this invention. Therefore, such a T cell response may be generated, accelerated, prolonged or enhanced via various methods known in the art of immunology and vaccination. An immune response may be raised or boosted against one or more viral antigens, in particular HPV early antigens, although antigens from other viruses and (myco)bacterial antigens may also be used or even combined. Particularly preferred are the use of one or more HPV early antigens selected from the HPV early proteins E2, E6 and E7 from high risk types. Many CTL and T-helper epitopes, capable of inducing T cell responses by IFN-γ ELISPOT assays have been identified by the current inventors (WO 02/070006). Preferred is the use of peptides of a specific length, long enough to avoid direct binding in the MHC groove. Longer peptides, preferably longer than about 12, more preferably about 15, 18, and most preferably from 22 up to 45 amino acids, require processing and are large enough to be taken up and processed internally by professional antigen presenting cells, such as dendritic cells. Preferred epitope comprising peptides from the HPV16 E7 protein comprise amino acid stretches 1-22 31-52, 41-62, 43-77, 51-72 and 77-98 of SEQ ID No.1. Preferred epitope comprising peptides from the HPV16 E2 protein comprise amino acid stretches 31-75, 91-120, 151-195, 271-300, 286-315, 301-330, 316-345 and 331-365 of SEQ ID No. 2. Preferred epitope comprising peptides from the HPV16 E6 protein comprise amino acid stretches 31-52, 81-102, 91-112, 111-132, 121-158 and 131-152 of SEQ ID No. 3. The choice of suitable peptides and viral epitopes comprised therein does not depend on the HLA type of the subject to be treated but will, among other factors, depend on the particular viral infections it carries. The skilled person will be able to readily find and substitute the amino acid stretches of these HPV16 peptides for the corresponding peptides from other high risk and highly homologous HPV types.

The administration of viral antigens in order to elicit a T-cell response, in particular a CD4+ T cell response, may be combined with the administration of CD40 receptor and/or 4-1-BB receptor activating compounds or agonists. These may be selected from known compounds, such as various natural or synthetic ligands of these receptors and/or (agonistic) antibodies or fragments and derivates thereof, as described in WO 03/084999, in order to enhance and/or prolong an immune response of peptide vaccination by the activation of dendritic cells, which will aid in the building up of a local inflammatory response.

Typically before or after determining whether a CD4+ T cell response against viral antigens is present, treatment of subjects with intraepithelial disorders of the ano-genital tract according to the invention may consist of a first administration of antigens. This may for instance comprise an injection with one or more high risk HPV E2, E6 and/or E7 antigens, preferably comprising peptides with epitopes as described above, which may be adminstered either alone or in different pharmaceutical compositions comprising various adjuvants known per se. Preferably a vaccination scheme is used which results in a strong HPV early-antigen-specific T-cell response, preferably of CD4+ T cells of type 1, that is in particular associated with the antigen-specific production of interferon-γ. Vaccination schemes and the use of adjuvants is known in the art and are readily available through the literature reported in the online PubMed database and may for instance also be found in Current Protocols in Immunology, Wiley Interscience 2004. At the peak of the T-cell response, comprising a strong CD4+ T cell response, which in general is about 1-2 weeks (but not limited to this period) after the last vaccination, the immune modifying agent or agents are applied locally in or on the lesions to be treated. The immune modifying agent, preferably an inflammation inducing agent as described herein before may be applied topically by various methods known to the skilled physician. This may for instance be carried out by using an ointment or cream, or applied with transdermal patches or may be injected in or around or nearby the intraepithelial lesion to be treated. At regular intervals thereafter the immune modifying agent(s) is applied locally in order to sustain the local inflammation until the lesion has disappeared. Optionally, booster doses of the viral antigens may be administered during this treatment to prolong or to enhance the T-cell response and improve the clinical outcome of the treatment. Alternatively, local application of immune modifying, or preferably inflammation inducing agents, precedes and/or takes place during and/or after the immunization/vaccination procedures.

The current invention also provides for new medicaments for use in the method of treatment according to this invention. Formulation of medicaments, ways of administration and the use of pharmaceutically acceptable excipients are known and customary in the art and for instance described in Remington; The Science and Practice of Pharmacy, 21$^{nd}$ Edition 2005, University of Sciences in Philadelphia. Pharmaceutical compositions and medicaments of the invention may thus comprise binders such as lactose, cellulose and derivatives thereof, polyvinylpyrrolidone (PVP), humectants, disintegration promoters, lubricants, disintegrants, starch and derivatives thereof, sugar solubilizers, immuno-stimulatory adjuvants or other excipients. The invention provides methods and means to formulate and manufacture new medicaments and/or pharmaceutical formulations for the treatment of anogenital intraepithelial neoplasias and/or infections of these epithelia in subjects scoring positive for a T-cell response against viral antigens such as HPV, CMV and HSV antigens, in particular high risk HPV early antigens. Medicaments according to this invention comprise as an active component an immune modulating compound, capable of inducing a local inflammatory response, and are preferably Toll like receptor activating compounds, capable of activating TLR's 1 to 10, and most preferably a TLR-3, TLR-7 and/or TLR-9 activating compounds. TLR activating compounds which are highly suitable for use in pharmaceutical compositions and medicaments according to the invention comprise bacterial lipoproteins and acetylated forms thereof, bacterial glycolipids, bacterial outer membrane proteins, bacterial heatshock proteins, bacterial flagellae or flagellins, fimbriae, group B *Streptococcus* heat labile soluble factor (GBS-F), *Staphylococcus* modulins, Gram positive LPS or lipid A, LTA, Gram negative LPS or LTA, mycobacterial lipoarabinomannans, mycobacterial lipoproteins, unmethylated CpG DNA, chromatin-IgG complexes, dsRNA, poly(I:C), viral coat or envelope proteins, taxol or derivatives thereof, hyaluronan containing oligosaccharides, fibronectins, imidazoquinolines and heat shock proteins from the host organism. In particular dsRNA, poly(I:C), unmethylated CpG DNA and other substances which trigger TLR3 and TLR9. Most preferably TLR7 activating compounds are used, such as but not limited to Imidazoquinolines (for example Imiquimod and/or R-848/resiquimod), loxoribine (7-allyl-8-oxoguanosine), bropirimine (2-amin-5-allyl-8-oxoguanosine) and derivatives and analogues thereof. Imidazoquinolines are the most highly preferred compounds for use according this invention.

A pharmaceutical composition according to the invention may optionally comprise one or more compounds capable of further stimulating a local inflammatory response, such as chemokines and cytokines that are part of the inflammatory pathway or cascade. Examples are the use of the type 1 interferons (α and β) and the cytokines IL-1, TNF-α, IL-6, IL-8 (CXCL8) and IL-12 or the chemokines CXCL1,2,3,7,8, 10,12,13; CCL2,3,4,5, 11, 18, 20, 27; XCL1 and CX3CL1. Also substances and compounds capable of stimulating production of these cytokines and chemokines in situ may also be advantageously admixed to the pharmaceutical compositions and medicaments of this invention.

In yet another embodiment the invention comprises a kit of parts, comprising one or more, preferably at least two, components selected from:

an immune modifying agent, preferably an inflammation inducing agent, a compound or a composition capable of further stimulating a local inflammatory response comprising chemokines and/or cytokines, an HPV vaccine comprising HPV derived peptides, and/or HPV peptides and reagents for the detection of a cellular immune response against HPV.

Definitions

Intraepithelial neoplasia is precancerous cell growth, a synonym for dysplasia. Cervical Intraepithelial Neoplasia (abbreviated "CIN") is a cervical condition caused by a sexually transmittable viruses such as low or high risk Human Papilloma Viruses. CIN is also called Cervical Dysplasia. CIN is classified as I, II or III depending on its severity. It is considered a pre-cancerous abnormality. The mildest form, CIN I rarely progresses to cancer. The more severe forms, CIN II and CIN III can develop into malignancies if not treated adequately. Vulvar Intraepithelial Neoplasia (VIN) is the presence of abnormal cells in the vulvar skin. It can occur in one area or several areas in the vulvar skin at the same time. Also VIN occurs in three different degrees of severity or stages, similar to CIN. VAIN stands for vaginal intraepithelial neoplasias and is the analogous neoplasia in the vagina.

Male forms of intraepithelial neoplasias comprise Penile intraepithelial neoplasia (PIN). Penile intraepithelial neoplasia is a rare pre-cancerous disease of the outer skin layer (epidermis) of the penis. It is also referred to as Erythroplasia of Queyrat, Bowen's disease of the penis, in-situ squamous cell carcinoma of the penis or P.I.N. Lesions usually appear on the glans or inner aspect of the foreskin and are almost always found in uncircumcised men. If left untreated, 10-30% of cases develop into invasive squamous cell carcinoma (cancer) of the penis. Uncircumcised males over 50 years of age are most at risk of getting penile intraepithelial neoplasia, although it may rarely occur in younger men. Penile intraepithelial neoplasia is associated with chronic infection with human papilloma virus (HPV), the cause of genital warts, and immune suppression by medications or disease.

Anal intraepithelial neoplasia (AIN) occurs both in men and women and is believed to be a precursor of anal squamous cell cancer. Its incidence is rising in high-risk groups, particularly those infected with the human immunodeficiency virus (HIV). The aetiology of AIN is intricately linked with human papilloma viruses, although a role for infection or co-infection with other viruses is not excluded. There is yet no standard management for AIN and this is mainly due to difficulties in both diagnosis and treatment. A variety of treatment options have been tried with varying success. Surgery is associated with significant recurrence, particularly in HIV-positive patients.

Intraepithelial neoplasia is also referred to as squamous intraepithelial lesions, for which low grade and high grade forms are distinguished, analogous to VIN, CIN, PIN, VAIN or AIN stage I or stages II-III respectively.

FIGURE LEGENDS

FIG. 1

A, freshly isolated peripheral blood mononuclear cells from 20 patients with high-grade HPV16-associated VIN were tested in short-term proliferation assays using a complete set of HPV16 E2, E6, and E7-derived peptide pools. Responses were scored positive when the proliferation (cpm) of $\geq 6$ of 8 test wells exceeded the mean proliferation+3×SD of the control (medium only) wells, and the mean stimulation index of all test wells over control wells was $\geq 3$. Memory response mix (MRM), consisting of a mixture of recall antigens, was used as a positive control. The stimulation indices of responses scored positive are indicated.

B, supernatants of the positive proliferative responses indicated in A were analyzed for the presence of IFNγ, tumor necrosis factor α, IL-2, IL-4, IL-5, and IL-10 by cytometric bead array. The indicated layout is used for the six measured cytokines; a filled square represents antigen-specific cytokine production. Cut-off values were based on the standard curves of the different cytokines (50 pg/ml for IFNγ and 10 pg/ml for the remaining cytokines). Antigen-specific cytokine production was defined as a cytokine concentration above cut-off level and >2× the concentration of the medium control.

FIG. 2

A and B, Human papillomavirus 16-specific IFNγ-producing T-cell responses in 2 representative patients with high-grade VIN (#2, left and 10, right). T-cell responses are shown at week 0 (before imiquimod treatment), week 8 (during imiquimod treatment) and at week 16 (after imiquimod treatment). Local application of 5% imiquimod containing cream does not result in enhanced systemic HPV16-specific T-cell responses. Note that the magnitude of the T-cell responses varies slightly over the different time points. The mean number of spots and SE induced by the medium control or the peptides present in the E2, E6 and E7 pools per 100,000 PBMC are depicted. As positive control, the memory recall mix (MRM) was used. C and D, Patients with pre-existing HPV16-specific T-helper type 1 responses show objective clinical responses after imiquimod treatment. A typical example is shown. C, biopsy-proven VIN3 lesion of patient #5 before imiquimod treatment; D, the same vulvar area of patient #5 after 16 weeks of treatment.

FIG. 3

IgG and IgA reactivity to HPV16 VLPs over time in 17 VIN3 patients treated with imiquimod. At least two serum specimens were tested in every patient. Serological responses are shown at week 0 (before imiquimod treatment), week 8 (during imiquimod treatment) and at week 16 (after imiquimod treatment). The OD values are depicted as median ±SD of positive responses. The OD values were calculated by subtraction of the background response value and the mean OD value of the young children's sera.

EXAMPLES

Methods and Materials

Patients

Twenty-nine women with high-grade VIN (age range, 24-73 years; median age, 47 years) were recruited from the departments of gynecology of the Academic Medical Center, and Leiden and Erasmus University Medical Center, The Netherlands. On the average, these patients had been diagnosed with VIN3 5,4 years before enrollment in the study (range, 6 months-15 years). Eighteen women had undergone previous treatments for VIN3 (surgical excision, laser therapy or imiquimod treatment (#21, 24, 27)) before study entry.

Seventeen of these 29 subjects (age 29-60 years, median 43 years) were experimentally treated with a 5% imiquimod cream. The patients were asked to apply the cream to the affected areas on the vulva twice weekly overnight for a maximum period of 16 weeks. In order to analyze the effect of imiquimod treatment on the HPV16-specific immune response, we collected serial blood and serum samples before the start of imiquimod treatment (T=0), after 8 weeks of treatment (T=8), and at the end of treatment (T=16). Vulvar lesions were assessed by direct measurement and photographic records at entry, and after 8 and 16 weeks of treatment. Clinical responses were defined as a complete response (CR), a partial response type1 (PR1), as defined by a reduction in lesion diameter from 76-99%, a partial response type2 (PR2), as defined by a reduction in lesion diameter from 26-75%, or no clinical response.

From 20 of 29 women peripheral blood mononuclear cells (PBMCs) were isolated and directly used in order to analyze HPV16-specific proliferative T-cell reactivity. Of these 20 women, 8 patients had also participated in the imiquimod study. In 6 cases blood was taken 3 months (#1), 4 months (#10), 10 months (#5) to over 1 year (#12, 13 and 15) after the end of the imiquimod study, in the other 2 cases (# 2, 4) blood was taken within 4 weeks after the start of treatment. Serum was collected to study the presence of virus-like particle (VLP) L1-specific antibodies.

All subjects were typed for HPV by GP5+/6+PCR followed by reverse line blot analysis as described previously (26). The study design was approved by the Medical Ethical Committees and all women gave written informed consent.

Antigens

A set of peptides spanning the whole HPV 16 E2, E6 and E7 protein were used for the T-cell proliferation assays. The E2 peptides consisted of twenty-two 30-mer peptides with a 15-amino acid overlap and the COOH-terminal peptide with a length of 35 amino acids. For the T-cell proliferation assays, the E2 peptides, 32-mer peptides of the E6 protein, and the 35-mer peptides of the E7 protein with an overlap of 14 amino acids were used in pools of two peptides per pool. For the IFNγ ELISPOT assays, the peptides used spanned the HPV 16 E2, E6 and E7 protein and consisted of the most immunogenic regions of the E2 30-mer peptides (22) and fifteen E6 and nine E7 overlapping 22-mer peptides. The peptides were synthesized and dissolved as described previously (27). The peptide pools are indicated by the first and last amino acid of the region in the protein covered by the two peptides (e.g., E21-45, residues 1-30 and 16-45). Memory response mix (MRM), consisting of a mixture of tetanus toxoid (0.75 limus flocculentius/ml final concentration; National Institute of Public Health and Environment, Bilthoven, The Netherlands), *Mycobacterium tuberculosis* sonicate (2.5 µg/ml; generously donated by Dr P. Klatser, Royal Tropical Institute, Amsterdam, The Netherlands) and *Candida albicans* (0.005%, HAL Allergenen Lab. Haarlem, The Netherlands), was used as a positive control.

Short-Term T-Cell Proliferation Assay

Freshly isolated PBMCs were incubated with 12 pools of HPV16 E2-derived 30-mer peptides, 4 pools of E6 32-mer peptides, and 2 pools of E7 35-mer peptides (each pool consisted of two overlapping peptides). PBMCs were seeded at a density of $1.5 \times 10^5$ cells/well in a 96-well U-bottomed plate (Costar, Cambridge, Mass.) in 125 µl of Iscove's medium (BioWhittaker) supplemented with 10% autologous serum. HPV16 E2-, E6-, and E7-derived peptides were added at a concentration of 10 µg/ml/peptide. Medium alone was taken along as a negative control, and MRM (dilution, 1:50) served as a positive control. For each peptide pool, eight parallel microcultures were incubated. Fifty µl of supernatant from the microcultures was taken at day 6 after incubation and stored at −20° C. until cytokine analysis. Peptide-specific proliferation was measured at day 7 by [3H]-thymidine incorporation. Cultures were scored positive when the proliferation of ≧75% of the test wells exceeded the mean proliferation+3×SD of the control wells containing medium only, and the stimulation index, defined as the mean of all test wells divided by the mean of the control wells, was ≧3(22).

Analysis of Cytokines Associated with HPV 16-Specific Proliferative Responses

The detection of cytokines in the supernatants of the short-term proliferation assays was performed using the cytometric bead array (CBA) (Becton Dickinson). This technique allows the simultaneous detection of six different Th1 and Th2 cytokines IFNγ, tumor necrosis factor α, interleukin (IL)-2, IL-4, IL-5, and IL-10. The CBA was performed according to the manufacturer's instructions. Cut-off values were based on the standard curves of the different cytokines (100 pg/ml for IFNγ and 10 pg/ml for the remaining cytokines). Antigen-specific cytokine production was defined as a cytokine concentration above cut-off level and >2× the concentration of the medium control (23; 28).

Analysis of HPV 16-Specific T-Cell Reactivity by IFNγ Elispot

The number of IFNγ producing HPV-specific T-cells, present in the peripheral blood of the 17 patients treated with imiquimod, was quantified using ELISPOT that was performed as described previously (29; 30). Briefly, PBMC were thawed, washed and seeded at a density of $2 \times 10^6$ cells per well of a 24-well plate (Costar, Cambridge, Mass.) in 1 ml of IMDM (Bio Whittaker, Verviers, Belgium) enriched with 10% human AB serum, in the presence or absence of indicated HPV 16 E2, E6 and E7 peptide pools. Peptides were used in pools of 4-5 peptides at a concentration of 5 µg/ml/peptide. The peptides, as indicated by their first and last amino acid in the protein, were used in the following pools: E2-I: 1-30, 16-45, 31-60, 46-75; E2-II: 61-90, 76-105, 91-120, 106-135; E2-III: 121-150, 136-165, 151-180, 166-195; E2-IV: 271-300, 286-315, 301-330, 316-345, 331-365; E6-I: 1-22, 11-32, 21-42, 31-52; E6-II: 41-62, 51-72, 61-82, 71-92; E6-III: 81-102, 91-112, 101-122, 111-132; E6-IV: 111-132, 121-142, 131-152, 137-158; E7-I: 1-22, 11-32, 21-42, 31-52; E7-II: 41-62, 51-72, 61-82, 71-92, 77-98. Following 4 days of incubation at 37° C., PBMC were harvested, washed, and seeded in four replicate wells at a density of 105 cells per well in 100 µl IMDM enriched with 10% FCS in a Multiscreen 96-well plate (Millipore, Etten-Leur, The Netherlands) coated with an IFNγ catching antibody (Mabtech AB, Nacha, Sweden). Further antibody incubations and development of the ELISPOT was performed according to the manufacturer's instructions (Mabtech). Spots were counted with a fully automated computer-assisted-video-imaging analysis system (Bio Sys). Specific spots were calculated by subtracting the mean number of spots+2×SD of the medium control from the mean number of spots in experimental wells provided that the mean number of spots of the medium control wells were either <10 or >10 with a standard deviation <20% of the mean. Antigen-specific T-cell frequencies were considered to be increased when specific T-cell frequencies were ≧1/10,000 and at least ≧2× background. (30). The background number of spots was 2.6±2.2 (mean±SD), with one exception (#23, 51±10 spots).

HPV16 VLP ELISA

For the detection of HPV16-specific antibodies in serum we used an ELISA method previously described by Kirnbauer et al (31). Each serum sample was tested for reactivity against HPV16 virus-like particles (VLP, baculovirus-expressed capsids comprising the L1 protein) and against bovine papillomavirus (BPV) capsids, the latter disrupted by treatment with 0.1M carbonate buffer to serve as a negative control. Both VLP and BPV were kindly provided by Prof. dr. J. Dillner (LUNDS University, Sweden). The patients were tested for both HPV16-specific IgG and IgA. A set of sera of healthy children (n=8, mean age 7.3 years, range 4.3-14.1 years) was tested to determine background reactivity. For HPV16 L1-VLP IgG type responses a cut-off OD value of 0.230 was used (mean OD=0.060; range −0.056 to 0.150; mean+2 times standard deviation=0.230). For IgA type responses a cut-off of OD=0.215 was used (mean OD=0.189; range 0.171 to 0.205).

Statistical Analysis

Statistical analysis of the HPV16-specific proliferative responses associated with cytokine production was performed using Fisher's exact test. Fisher's Exact test (2-tailed) was used to analyze HPV-specific immunity to clinical response upon treatment with imiquimod. Statistical analyzes were performed using Graphpad Instat Software (version 3.0).

Example 1

HPV 16-specific cellular and humoral responses in patients with high grade VIN VIN forms a unique aspect of HPV-induced disease because patients are frequently treated, but the infection often persists. HPV-16 is found most often. To gain a more profound insight in the CD4+ T-cell response against HPV16 in VIN, we charted the magnitude, specificity and functionality of HPV16 E2, E6 and E7-specific proliferative T-cell responses in a group of 20 women with HPV16-associated high grade VIN.

Figure 1B:
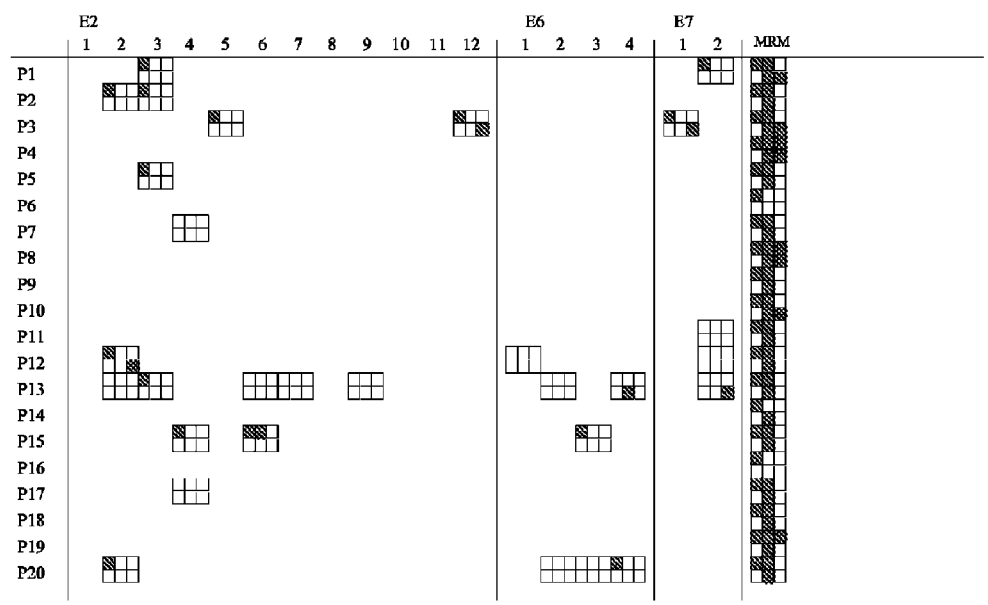

PBMC isolated from VIN patients were stimulated with peptides derived from HPV16 proteins E2, E6 and E7 as well as with a mix of common recall antigens (MRM), in a short-term proliferation assay. We have previously shown that this assay is geared towards the detection of CD4+ T-cell responses (23). HPV16-specific proliferative T-cell responses against E2 and/or E6 were detected in 10/20 patients (FIG. 1A). E7-specific responses were detected in 5/20 subjects. Analysis of the supernatants of these T-cell cultures for the presence of type 1 and type 2 cytokines revealed the secretion of the Th1 cytokine IFNγ in 8/20 patients. In some of the patients the production of TNFα, IL-5 and IL-10 was occasionally detected (FIG. 1B). Although the overall frequency of proliferative responses is similar when compared to that previously found for cervical cancer patients, the number of patients with IFNγ-associated HPV-specific T-cell responses in these VIN patients was higher (8/20 vs 4/17, respectively (23)).

In addition to T-cell immunity, the humoral response to HPV16 was measured in 28 VIN patients by ELISA using HPV16 L1-VLP as antigen. Overall, HPV16 L1-VLP IgG and IgA antibodies were detected in 25 of 28 (89%) and 13 of 28 (46%) subjects, respectively (Table 1). Based on the OD values, the HPV16 L1-VLP-specific IgG response exceeded that of IgA (Table 1). In general, HPV16-specific IgA responses were detected when patients displayed relatively high levels of HPV16-specific IgG. If IgG OD values were ≧0.5, 11/19 (58%) of the samples contained HPV16 L1-specific IgA, whereas at IgG levels <0.5 only ⅔ samples were IgA seropositive.

In conclusion, HPV16 L1-specific humoral immunity was detected in the great majority of patients, whereas HPV16 E2-, E6- and/or E7-specific IFNγ-associated type 1 T-cell reactivity was detected in about half of the patients tested.

Example 2

HPV16-specific immunity is associated with a more favorable clinical response upon immunomodulatory treatment with Imiquimod Our analysis of HPV16-specific proliferation indicates that a high number of the proliferative T-cell responses is associated with IFNγ production. To examine the role of these HPV16-specific type 1 T cell responses in the success or failure of treatment with the immunomodulator imiquimod, we studied this immune response in a group of patients with high-grade HPV16+VIN. PBMC were isolated before (T=0), during (T=8), and after (T=16) treatment, and stored in liquid nitrogen. HPV-specific T-cell reactivity against HPV16 peptides E2, E6 and E7 was analyzed by IFNγ ELISPOT. This is a sensitive method for the analysis of antigen-specific type 1 T-cell reactivity on frozen material (32; 33). Three of these patients had been treated with imiquimod in the year before inclusion in our study (Table 2, #21, 24 and 27). Of these 17 patients, 15 were HPV16-positive. Pre-existing IFNγ-associated T-cell responses (T=0) were detected in 8 of 15 patients by IFNγ ELISPOT. In 5/15 patients, HPV16-specific T-cell reactivity against E2 was detected, whereas 4/15 patients displayed a response against E6 (Table 2). None of these patients showed pre-existing T-cell responses against HPV16 E7. In 2 cases the T=0 sample was not available and the reaction in PBMC from T=8 are shown (Table 2, #1 and 22).

Figure 2A:
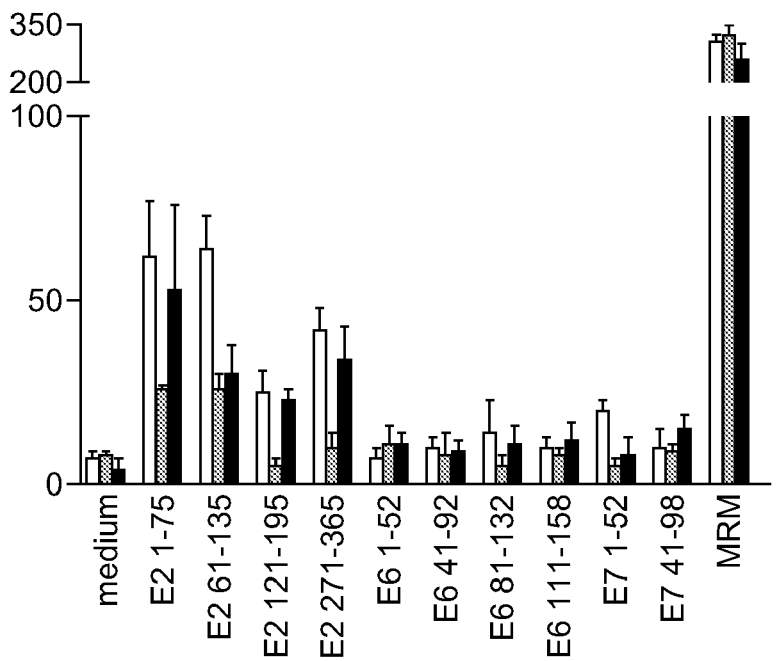
Figure 2B:
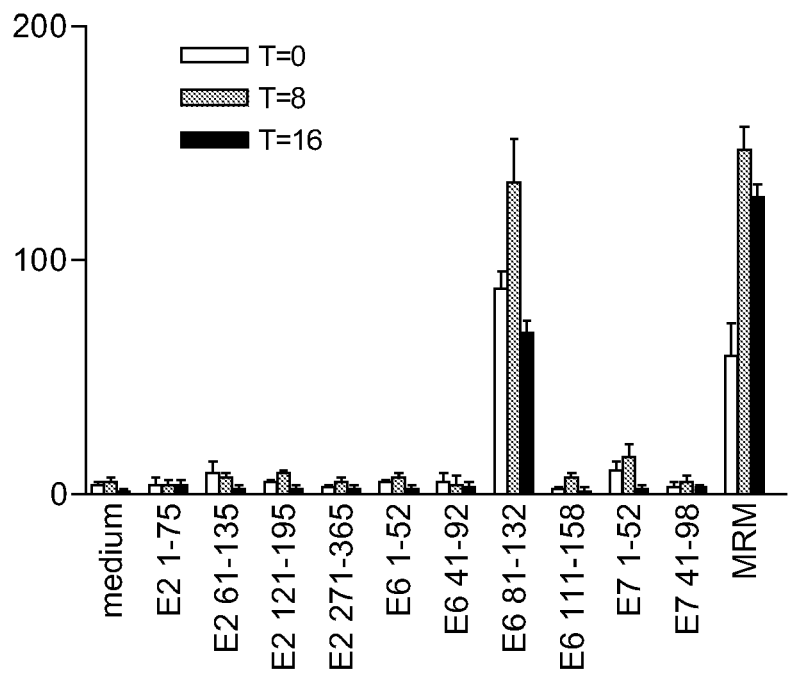
Figure 3:
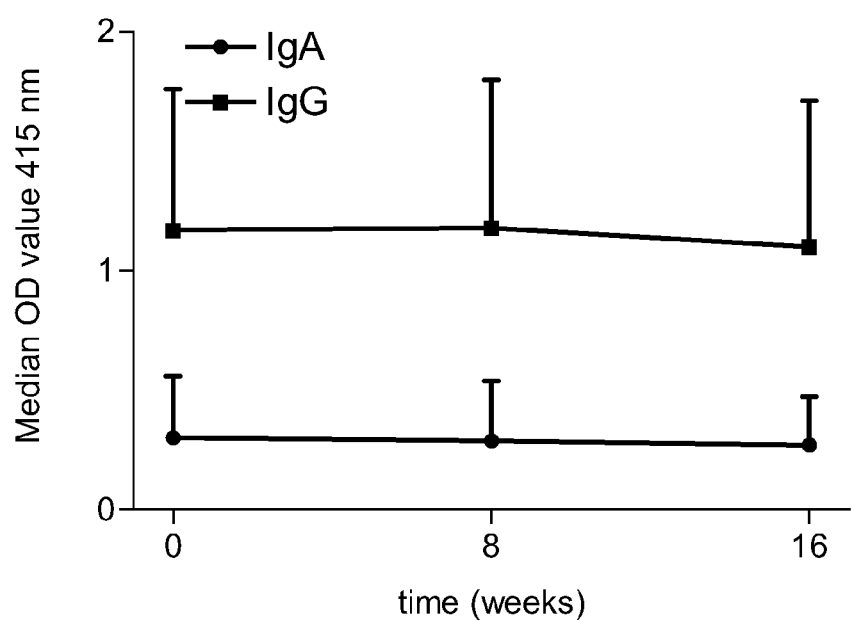

Despite that for some patients one of the two follow-up samples were not available (#5, 13, 27, 28), it was clear that we could not detect a direct influence of imiquimod on the numbers of HPV-specific T-cells. In none of the patients a clear-cut increase of HPV16-specific T-cells was detected upon imiquimod treatment (FIG. 2ab). In some cases patients had already been treated with a course of imiquimod before this study, but even this repeated treatment did not result in an increase of HPV 16 specific T-cells (Table 2, #21 and 24). Also, the HPV16 VLP-specific IgG and IgA response did not overly change when patients were treated with imiquimod (FIG. 3).

Figure 2C:
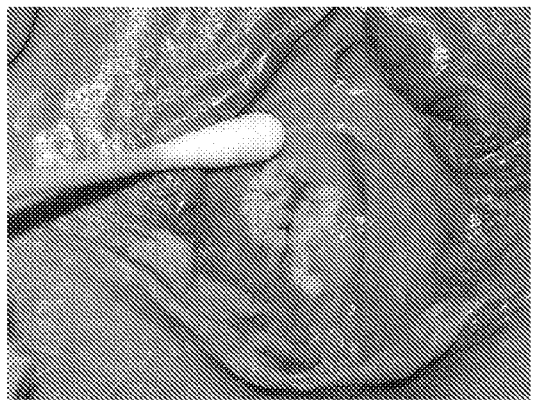
Figure 2D:

Thirteen of the 17 women treated (76%) displayed an overt clinical response upon treatment with imiquimod as indicated by 76-100% reduction in the size of their lesion (CR or PR1, Table 2 and FIG. 2cd). Three patients showed no reduction in size of the affected area of vulvar disease, and one woman showed only minimal improvement upon treatment.

Importantly, when the group of HPV16+patients (n=15) was divided in patients either with or without an HPV-specific Th1 immune response, all 8 patients with an HPV-specific immune response displayed a complete or near complete clinical response (CR or PR1) upon imiquimod treatment (Table 2). In contrast, patients without an HPV-specific immune response were less likely to show such a clinical improvement (p=0.03, 2-sided Fisher's exact test).

Taken together, chronic viral antigen exposure can induce type 1 CD4+ T-cell immunity against the HPV16 early antigens E2, E6 or E7 in patients with VIN3. The presence of these HPV16-specific Th1 cells as detected by IFNγ ELISPOT, even though not essential for imiquimod-induced regression of VIN lesions, does increase the likelihood of a strong clinical response. The presence of L1-specific humoral reactivity was not correlated with imiquimod-induced regressions.

REFERENCES

1. Burk R D, Kelly P, Feldman J, et al. Declining prevalence of cervicovaginal human papillomavirus infection with age is independent of other risk factors. Sex Transm Dis 1996; 23:333-41.

2. Koutsky L. Epidemiology of genital human papillomavirus infection. Am J Med 1997; 102:3-8.

3. Schiffman M, Kjaer S K. Chapter 2: Natural history of anogenital human papillomavirus infection and neoplasia. J Natl Cancer Inst Monogr 2003; 14-9.

4. Evander M, Edlund K, Gustafsson A, et al. Human papillomavirus infection is transient in young women: a population-based cohort study. J Infect Dis 1995; 171:1026-30.

5. Ho G Y, Bierman R, Beardsley L, Chang C J, Burk R D. Natural history of cervicovaginal papillomavirus infection in young women. N Engl J Med 1998; 338:423-8.

6. Remmink A J, Walboomers J M, Helmerhorst T J, et al. The presence of persistent high-risk HPV genotypes in dysplastic cervical lesions is associated with progressive disease: natural history up to 36 months. Int J Cancer 1995; 61:306-11.

7. Kjaer S K, van den Brule A J, Paull G, et al. Type specific persistence of high risk human papillomavirus (HPV) as indicator of high grade cervical squamous intraepithelial lesions in young women: population based prospective follow up study. BMJ 2002; 325:572.

8. van Beurden M, ten Kate F J, Smits H L, et al. Multifocal vulvar intraepithelial neoplasia grade III and multicentric lower genital tract neoplasia is associated with transcriptionally active human papillomavirus. Cancer 1995; 75:2879-84.

9. Buscema J, Naghashfar Z, Sawada E, Daniel R, Woodruff J D, Shah K. The predominance of human papillomavirus type 16 in vulvar neoplasia. Obstet Gynecol 1988; 71:601-6.

10. Hording U, Junge J, Poulsen H, Lundvall F. Vulvar intraepithelial neoplasia III: a viral disease of undetermined progressive potential. Gynecol Oncol 1995; 56:276-9.

11. Sykes P, Smith N, McCormick P, Frizelle F A. High-grade vulvar intraepithelial neoplasia (VIN 3): a retrospective analysis of patient characteristics, management, outcome and relationship to squamous cell carcinoma of the vulva 1989-1999. Aust N Z J Obstet Gynaecol 2002; 42:69-74.

12. Andreasson B, Bock J E. Intraepithelial neoplasia in the vulvar region. Gynecol Oncol 1985; 21:300-5.

13. Rettenmaier M A, Berman M L, DiSaia P J. Skinning vulvectomy for the treatment of multifocal vulvar intraepithelial neoplasia. Obstet Gynecol 1987; 69:247-50.

14. Schon M P and Schon M. Immune modulation and apoptosis induction: two sides of the antitumoral activity of imiquimod. Apoptosis 2004; 9:291-8.

15. Geisse J, Caro I, Lindholm J, et al. Imiquimod 5% cream for the treatment of superficial basal cell carcinoma: results from two phase III, randomized, vehicle-controlled studies. Am Acad Dermatol 2004; 50:722-33.

16. Sauder D N. Imiquimod: modes of action. Br J Dermatol 2003; 149 Suppl 66:5-8.

17. Stanley M A. Imiquimod and the imidazoquinolones: mechanism of action and therapeutic potential. Clin Exp Dermatol 2002; 27:571-7.

18. Marchitelli C, Secco G, Perrotta M, Lugones L, Pesce R, Testa R. Treatment of bowenoid and basaloid vulvar intraepithelial neoplasia 2/3 with imiquimod 5% cream. J Reprod Med 2004; 49:876-82.

19. Todd R W, Etherington I J, Luesley D M. The effects of 5% imiquimod cream on high-grade vulvar intraepithelial neoplasia. Gynecol Oncol 2002; 85:67-70.

20. van Seters M, Fons G, van Beurden M. Imiquimod in the treatment of multifocal vulvar intraepithelial neoplasia 2/3. Results of a pilot study. J Reprod Med 2002; 47:701-5.

21. Wendling J, Saiag P, Berville-Levy S, Bourgault-Villada I, Clerici T, Moyal-Barracco M. Treatment of undifferentiated vulvar intraepithelial neoplasia with 5% imiquimod cream: a prospective study of 12 cases. Arch Dermatol 2004; 140:1220-24.

22. de Jong A, van der Burg S H, Kwappenberg K M, et al. Frequent detection of human papillomavirus 16 E2-specific T-helper immunity in healthy subjects. Cancer Res 2002; 62:472-9.

23. de Jong A, van Poelgeest M I, van der Hulst J M, et al. Human papillomavirus type 16-positive cervical cancer is associated with impaired CD4+ T-cell immunity against early antigens E2 and E6. Cancer Res 2004; 64:5449-55.

24. Welters M J, de Jong A, van den Eeden S J, et al. Frequent display of human papillomavirus type 16 E6-specific memory T-helper cells in the healthy population as witness of previous viral encounter. Cancer Res 2003; 63:636-41.

25. Palefsky J M, Holly E A. Chapter 6: Immunosuppression and co-infection with HIV. J Natl Cancer Inst Monogr 2003; 41-6.

26. van den Brule A J, Pol R, Fransen-Daalmeijer N, Schouls L M, Meijer C J, Snijders P J. GP5+/6+PCR followed by reverse line blot analysis enables rapid and high-throughput identification of human papillomavirus genotypes. J Clin Microbiol 2002; 40(3):779-87.

27. van der Burg S H, Kwappenberg K M, Geluk A, et al. Identification of a conserved universal Th epitope in HIV-1 reverse transcriptase that is processed and presented to HIV-specific CD4+ T-cells by at least four unrelated HLA-DR molecules. J Immunol 1999; 162:152-60.

28. van der Burg S H, Menon A G, Redeker A, et al. Magnitude and polarization of P53-specific T-helper immunity in connection to leukocyte infiltration of colorectal tumors. Int J Cancer 2003; 107:425-33.

29. de Jong A, O'Neill T, Khan A Y, et al. Enhancement of human papillomavirus (HPV) type 16 E6 and E7-specific T-cell immunity in healthy volunteers through vaccination with TA-CIN, an HPV 16 L2E7E6 fusion protein vaccine. Vaccine 2002; 20:3456-64.

30. van der Burg S H, Ressing M E, Kwappenberg K M, et al. Natural T-helper immunity against human papillomavirus type 16 (HPV16) E7-derived peptide epitopes in patients with HPV16-positive cervical lesions: identification of 3 human leukocyte antigen class II-restricted epitopes. Int J Cancer 2001; 91:612-18.

31. Kimbauer R, Hubbert N L, Wheeler C M, Becker T M, Lowy D R, Schiller J T. A virus-like particle enzyme-linked immunosorbent assay detects serum antibodies in a majority of women infected with human papillomavirus type 16. J Natl Cancer Inst 1994; 86:494-9.

32. Baldwin P J, van der Burg S H, Boswell C M, et al. Vaccinia-expressed human papillomavirus 16 and 18 e6 and e7 as a therapeutic vaccination for vulvar and vaginal intraepithelial neoplasia. Clin Cancer Res 2003; 9:5205-13.

33. Smyth L J, van Poelgeest M I, Davidson E J, et al. Immunological responses in women with human papillomavirus type 16 (HPV-16)-associated anogenital intraepithelial neoplasia induced by heterologous prime-boost HPV-16 oncogene vaccination. Clin Cancer Res 2004; 10:2954-61.

34. Todd R W, Roberts S, Mann C H, Luesley D M, Gallimore P H, Steele J C. Human papillomavirus (HPV) type 16-specific CD8+ T-cell responses in women with high grade vulvar intraepithelial neoplasia. Int J Cancer 2004; 108:857-62.

35. Davidson E J, Sehr P, Faulkner R L, et al. Human papillomavirus type 16 E2- and L1-specific serological and T-cell responses in women with vulvar intraepithelial neoplasia. J Gen Virol 2003; 84:2089-97.

36. Todd R W, Steele J C, Etherington I, Luesley D M. Detection of CD8+ T-cell responses to human papillomavirus type 16 antigens in women using imiquimod as a treatment for high-grade vulvar intraepithelial neoplasia. Gynecol Oncol 2004; 92:167-74.

37. Bontkes H J, de Gruijl T D, van den Muysenberg A J, et al. Human papillomavirus type 16 E6/E7-specific cytotoxic T lymphocytes in women with cervical neoplasia. Int J Cancer 2000; 88:92-8.

38. Ressing M E, van Driel W J, Celis E, et al. Occasional memory cytotoxic T-cell responses of patients with human papillomavirus type 16-positive cervical lesions against a human leukocyte antigen-A*0201-restricted E7-encoded epitope. Cancer Res 1996; 56:582-8.

39. Nimako M, Fiander A N, Wilkinson G W, Borysiewicz L K, Man S. Human papillomavirus-specific cytotoxic T lymphocytes in patients with cervical intraepithelial neoplasia grade III. Cancer Res 1997; 57:4855-61.

40. Youde S J, Dunbar P R, Evans E M, et al. Use of fluorogenic histocompatibility leukocyte antigen-A*0201/HPV 16 E7 peptide complexes to isolate rare human cytotoxic T-lymphocyte-recognizing endogenous human papillomavirus antigens. Cancer Res 2000; 60:365-71.

41. Gul N, Ganesan R, Luesley D M. Characterizing T-cell response in low-grade and high-grade vulvar intraepithelial neoplasia, study of CD3, CD4 and CD8 expressions. Gynecol Oncol 2004; 94:48-53.

42. Abdel-Hady E S, Martin-Hirsch P, Duggan-Keen M, et al. Immunological and viral factors associated with the 43. Davidson E J, Boswell C M, Sehr P, et al. Immunological and clinical responses in women with vulvar intraepithelial neoplasia vaccinated with a vaccinia virus encoding human papillomavirus 16/18 oncoproteins. Cancer Res 2003; 63:6032-41.

44. Mota F, Rayment N, Chong S, Singer A, Chain B. The antigen-presenting environment in normal and human papillomavirus (HPV)-related premalignant cervical epithelium. Clin Exp Immunol 1999; 116:33-40.

45. Giannini S L, Hubert P, Doyen J, Boniver J, Delvenne P. Influence of the mucosal epithelium microenvironment on Langerhans cells: implications for the development of squamous intraepithelial lesions of the cervix. Int J Cancer 2002; 97:654-9.

46. Pao C C, Lin C Y, Yao D S, Tseng C J. Differential expression of cytokine genes in cervical cancer tissues. Biochem Biophys Res Commun 1995; 214:1146-51.

47. Matsumoto K, Leggatt G R, Zhong J, et al. Impaired antigen presentation and effectiveness of combined active/passive immunotherapy for epithelial tumors. J Natl Cancer Inst 2004; 96:1611-19.

48. van Mierlo G J, Boonman Z F, Dumortier H M, et al. Activation of dendritic cells that cross-present tumor-derived antigen licenses CD8+ CTL to cause tumor eradication. J Immunol 2004; 173:6753-59.

49. Villada I B, Barracco M M, Ziol M, et al. Spontaneous regression of grade 3 vulvar intraepithelial neoplasia associated with human papillomavirus-16-specific CD4(+) and CD8(+) T-cell responses. Cancer Res 2004; 64:8761-66.

50. Davidson E J, Faulkner R L, Sehr P, et al. Effect of TA-CIN (HPV 16 L2E6E7) booster immunisation in vulvar intraepithelial neoplasia patients previously vaccinated with TA-HPV (vaccinia virus encoding HPV 16/18 E6E7). Vaccine 2004; 22:2722-9.

51. Shizuo Akiro, Hiroaki Hemmi, Recognition of pathogen-associated molecular patterns by TLR family, Immunology Letters (85) 2003 p85-95.

---

The invention claimed is:

1. A method for treating anogenital intraepithelial neoplasia in a subject, comprising the steps of:
   (a) measuring or detecting the presence of a CD4+ type 1 T helper (Th1) cell response against an human papilloma virus (HPV) early antigen of HPV protein E2, E6 or E7 in said subject to ascertain whether the subject has a detectable CD4+ Th1cell response against said antigen; and
   (b) in a subject in whom said CD4+ Th1-cell response is detectable,
      (i) locally administering to or near a lesion of the neoplasia an effective amount of a Toll-like receptor-7 (TLR-7)-activating compound selected from the group consisting of imiquimod, R848/resiquimod, loxoribine and bropirimine, thereby inducing local inflammation, and,
      (ii) optionally, immunizing the subject with the early HPV antigen before, during or after the local administration of step (b)(i), to prolong or enhance the antigen-specific Th1cell response; or
   (c) in a subject in whom said CD4+ Th1cell response is undetectable, immunizing the subject with said early HPV antigen to elicit said antigen-specific Th1cell response and, concurrently or thereafter, locally administering to or near said lesion an effective amount of the TLR-7 activating compound, thereby inducing local inflammation,
   wherein the local inflammation produced by the local administration of the TLR-7 activating compound and the Th1cell response present in the subject, with or without said immunization of step (b)(ii) or (c), results in treatment of said neoplasia.

2. The method according to claim 1 wherein the neoplasia is vulvar intraepithelial neoplasia.

3. The method according to claim 1 further comprising administering locally to or near the lesion an interferon or other cytokine or chemokine that induces local inflammation or a pharmaceutical composition that induces local inflammation mediated by interferons, cytokines or chemokines.

4. The method according to claim 1, wherein the CD4+ Th1-cell response is detectable, and the subject is immunized with said early HPV antigen before or concurrently with said local administration in (b)(i).

5. The method according to claim 1 wherein the HPV early antigen used to immunize the subject and induce or enhance said CD4+ Th cell response is with is a peptide of 12 to 45 amino acids in length, from said HPV E2, E6 or E7 protein.

6. The method according to claim 5 wherein the peptide used to induce or enhance said CD4+ Th1cell response in the subject elicits an IFNγ response in Th1cells.

7. The method according to claim 1 wherein said immunization to induce or enhance said antigen-specific CD4+ Th1-cell response further comprises administering to the subject an effective amount of an agonistic antibody specific for CD40.

8. The method according claim 1, wherein said immunization to induce or enhance said antigen-specific CD4+ Th1-cell response further comprises administering to the subject an effective amount of an agonistic antibody specific for 4-1 BB.

9. The method according to claim 5 wherein the peptide is:
   (a) a peptide the sequence of which corresponds to residues 1-22, 31-52, 41-62, 43-77, 51-72 or 77-98 of SEQ ID NO:1;
   (b) a peptide the sequence of which corresponds to residues 31-75, 91-120, 151-195, 271-300, 286-315, 301-330, 316-345 or 331-365 of SEQ ID NO:2; or
   (c) a peptide the sequence of which corresponds to residues 31-52, 81-102, 91-112, 111-132, 121-158 or 131-152 of SEQ ID NO:3.

10. The method according to claim 4, wherein said immunization to enhance said antigen-specific CD4+ Th1-cell response comprises administering to the subject effective amounts of
    (i) an agonistic antibody specific for CD40; and/or
    (ii) an agonistic antibody specific for 4-IBB.

11. The method according to claim 1 wherein the TLR-7-activating compound is imiquimod.

* * * * *

SEQUENCE LISTING

```
<160> NUMBER OF SEQ ID NOS: 3

<210> SEQ ID NO 1
<211> LENGTH: 98
<212> TYPE: PRT
<213> ORGANISM: Human papillomavirus type 16

<400> SEQUENCE: 1

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 2
<211> LENGTH: 365
<212> TYPE: PRT
<213> ORGANISM: Human papillomavirus type 16

<400> SEQUENCE: 2

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
```

-continued

```
                65                  70                  75                  80
Thr Ile Tyr Asn Ser Gln Tyr Ser Asn Glu Lys Trp Thr Leu Gln Asp
                    85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285

Val His Leu Lys Gly Asp Ala Asn Thr Leu Lys Cys Leu Arg Tyr Arg
    290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
        355                 360                 365

<210> SEQ ID NO 3
<211> LENGTH: 158
<212> TYPE: PRT
<213> ORGANISM: Human papillomavirus type 16

<400> SEQUENCE: 3

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80
```

```
                                          -continued

Ser Glu Tyr Arg His Tyr Cys Tyr Ser Leu Tyr Gly Thr Thr Leu Glu
                85              90              95

Gln Gln Tyr Asn Lys Pro Leu Cys Asp Leu Leu Ile Arg Cys Ile Asn
            100             105             110

Cys Gln Lys Pro Leu Cys Pro Glu Glu Lys Gln Arg His Leu Asp Lys
        115             120             125

Lys Gln Arg Phe His Asn Ile Arg Gly Arg Trp Thr Gly Arg Cys Met
    130             135             140

Ser Cys Cys Arg Ser Ser Arg Thr Arg Arg Glu Thr Gln Leu
145             150             155
```